United States Patent [19]

Beiter

[11] Patent Number: 4,931,044
[45] Date of Patent: Jun. 5, 1990

[54] BLOOD COLLECTION VALVE

[75] Inventor: Werner Beiter, Dauchingen, Fed. Rep. of Germany

[73] Assignee: Becton, Dickinson and Company, Franklin Lakes, N.J.

[21] Appl. No.: 254,504

[22] Filed: Oct. 6, 1988

[30] Foreign Application Priority Data

Oct. 7, 1987 [DE] Fed. Rep. of Germany ....... 3733810

[51] Int. Cl.$^5$ ............................................. A61M 5/00
[52] U.S. Cl. ..................................... 604/248; 604/32; 604/236; 128/766; 251/149; 251/149.5; 251/149.9
[58] Field of Search ............... 604/32, 236, 169, 905, 604/248; 128/766; 251/149, 149.1, 149.2, 149.4, 149.9

[56] References Cited

U.S. PATENT DOCUMENTS

| | | | |
|---|---|---|---|
| 1,831,668 | 11/1931 | Juhl | 604/248 |
| 3,831,629 | 8/1974 | Mackal et al. | 137/525 |
| 3,896,853 | 7/1975 | Bernhard | 604/236 X |
| 3,897,810 | 8/1975 | Arnett et al. | 251/149.2 X |
| 3,920,002 | 11/1975 | Dye et al. | 251/149.4 |
| 4,366,816 | 1/1983 | Bayard et al. | 604/905 X |
| 4,387,879 | 6/1983 | Tauschinski | 604/247 |
| 4,468,225 | 8/1984 | Tcheraz | 604/248 |
| 4,842,591 | 6/1989 | Luther | 604/207 |

Primary Examiner—C. Fred Rosenbaum
Assistant Examiner—C. Maglione
Attorney, Agent, or Firm—Aaron Passman

[57] ABSTRACT

A blood collecting valve (10) is provided with a structural input part (11.1) with a half moon shaped separating wall opening (18) as well as a structural output part (12.1) which is rotatable with respect to the structural input part with a seal face opening (23). Both are disposed outside of the rotational axis of the associated structural parts. Thereby, it is possible to bring the two opening into congruence with each other by rotating around the rotational axis or to again sealingly separate the same from each other.

The mentioned common rotating of the structural input part and the structural output part and thereby the opening and closing of the blood collection valve may be performed by rotating a blood collecting cylinder (16) being inserted into the structural output part with an application conus (15). Hence, no separate manual handling is required for using the blood collection valve.

14 Claims, 3 Drawing Sheets

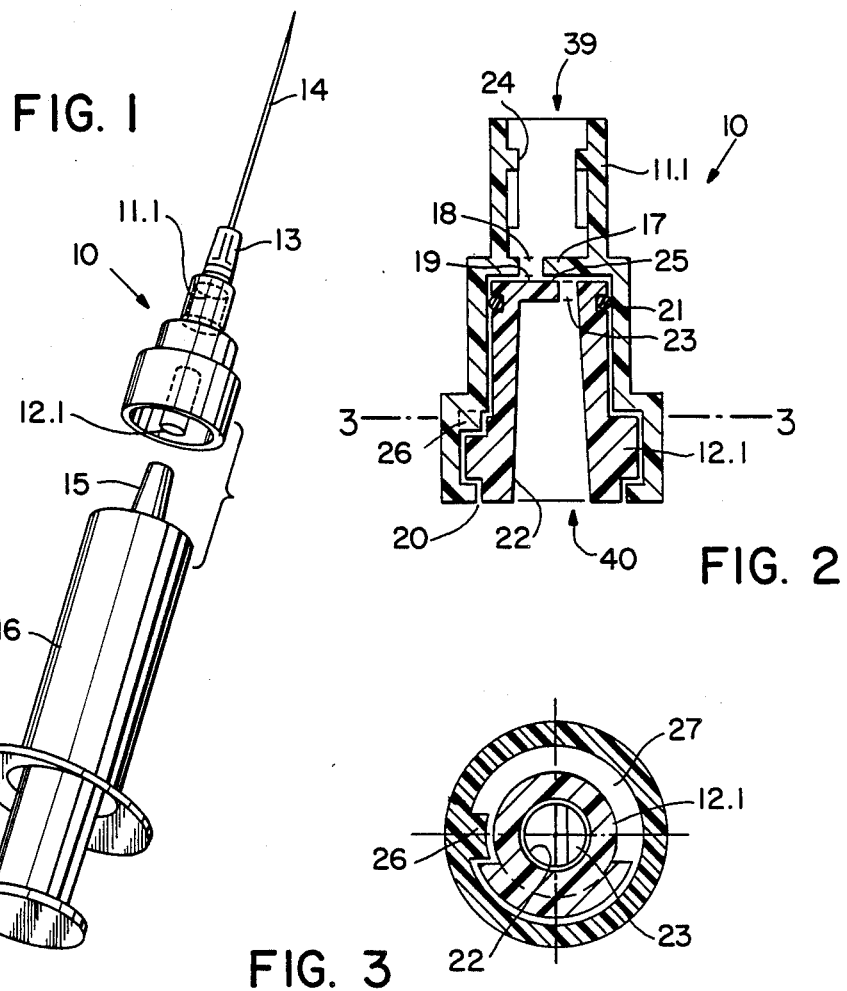
FIG. 1
FIG. 2
FIG. 3
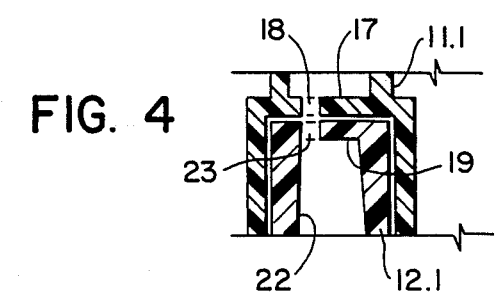
FIG. 4

FIG. 5
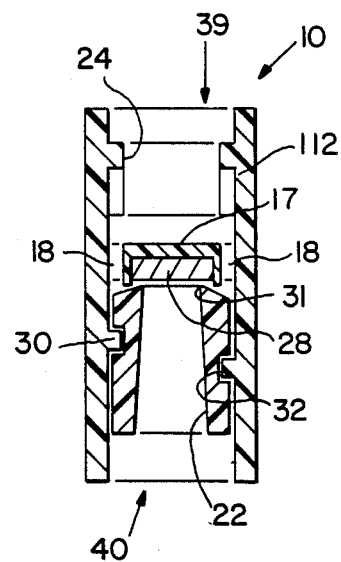
FIG. 7
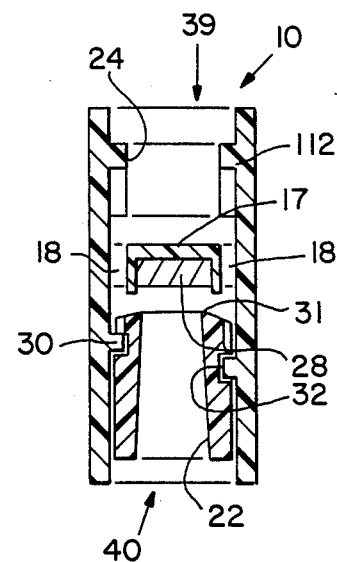
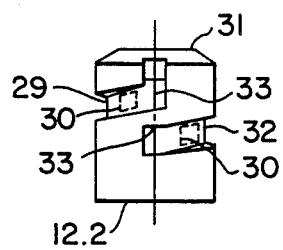
FIG. 6

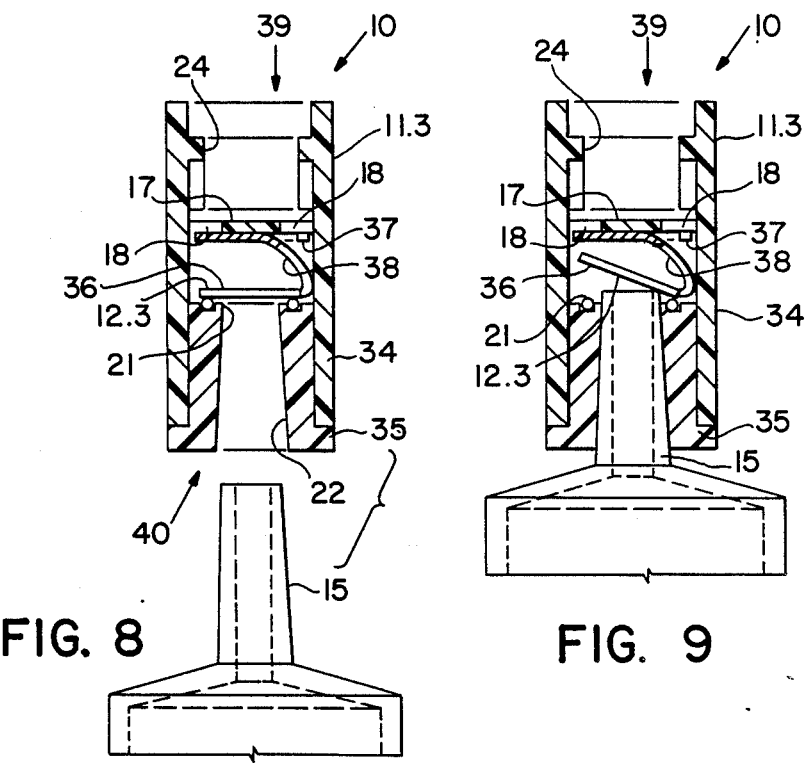
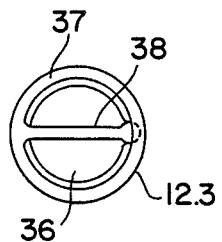

BLOOD COLLECTION VALVE

TECHNICAL FIELD

The invention relates to a blood collecting valve as it used for repeatedly taking blood from a patient from a blood taking location which had been applied to the patient for a temporary period of time. Such valves are also used when solutions have to be injected into the circulatory system of a patient

STATE OF THE ART

Each blood collection location which is applied for a temporary period of time is provided with a blood collecting device in form of a canula or a catheter. A capsule with a rubber membrane may be connected to this blood collecting device. For the purpose of collecting blood or for injecting of solutions the rubber membrane is penetrated by a canula which is mounted on an injection device like, for example, a blood collecting cylinder or an injection element. It is disadvantageous with such a device or devices, wherein a rubber membrane is penetrated by a canula, that rubber particles will get into the circulatory system which is extremely undesirable.

Therefore, instead of the mentioned structural parts with rubber membranes, preferably blood collection valves are used. The simplest embodiment a hose with a hose clamp is mounted on the input side on the aforementioned canula or the aforementioned catheter. The output conus of an injection device is placed into the output of the hose. As soon as the blood collecting line is closed to the outside in this manner, the hose valve will opened so that either blood may be collected or a solution may be injected. Thereafter the clamp is again closed and the injection device is removed. The disadvantage of this very simple embodiment is that a hose volume is present between the squeeze location of the connecting hose and the aforementioned output conus in which blood collects during the blood taking which drops out when removing the blood collecting cylinder. This is particularly undesirable when blood is taken from a person who is the carrier of an infectious disease which is transmitted by touching with or absorption of blood.

The aforementioned disadvantage is eliminated in blood collecting valves having a three-way stopcock. Here, the aforementioned output conus can be directly attached onto the valve closing location so that no more volume is available between the closing location and the output conus, which could later be filled with dropping out blood. However, three-way stopcocks are disadvantageous in that they are expensive and hard to handle. The three-way stopcock, like any other blood collecting valve must be permanently held manually during the blood taking or the injecting of solutions. With the other hand one must at first insert a blood collecting cylinder. This must then let go for opening the three-way stopcock. Then, again with the second hand blood is taken with the aid of the blood collecting cylinder. In order to close the valve, the second hand must again grip the stopcock and subsequently back to the cylinder so as to remove the same. Thereafter, if a solution is injected, an injection element is placed upon the three-way stopcock. The permanent alternation of the second hand between valve and placed syringe is repeated.

DESCRIPTION OF THE INVENTION

A blood collecting device in accordance with the invention is provided with an input structure and an output structure which are so shaped that during a common displacement with respect to each other in a first direction the input of the valve is connectable with the output and by displacement in the opposite direction the path between input and output is again closed.

Since the two structures are solid structures it is possible, like in the known three-way stopcock, to dispose the output conus of a mounted injection device, for example, a blood taking cylinder or an injection element in close proximity to the closing location, so that no blood-dead volume is present. The valve is directly actuated above the injection device being mounted above the output structure, in that with the aid of the injection device the output structure is displaced with respect to the input structure. Therefore, while using the injection device, during the opening of the valve, during actuation, during the closing of the valve and the removal it never is released.

The common displacement of the mentioned structural parts may be performed by twisting or linear displacements. During twisting as well as during a linear displacement the embodiment may be such that two passage openings each, one each in one each structure are brought into congruence with each other or be separated from each other. However, the twisting may have the effect that in view of a helical guiding the one structure with a valve element pushes onto a valve seat on the other structure or that a lifting of the valve element from the valve seat occurs, depending on the direction of screwing. Such a lifting and reseating of a valve element with respect to a valve seat may also occur by a linear displacement, preferably in that the valve body during the application of an injection device is pushed away by the output conus from the valve seat against the force of a spring and during the removal of the injection device is again pushed against the valve seat by the force of the spring. Thus, it is assured that the valve is safely closed, as long as no injection device is mounted.

SHORT DESCRIPTION OF THE DRAWINGS

FIG. 1 perspective explosion drawing of a blood collecting cylinder and a canula with intermediary switchable blood collection valve;

FIG. 2 longitudinal section through a blood collection valve with an input structure valve which is rotatable with respect to the output structure, in order to bring two openings in congruence with respect to each other or to again separate them from each other, in closed position;

FIG. 3 cross section along line 3—3 in FIG. 2;

FIG. 4 partial longitudinal section corresponding to FIG. 2, however illustrating the closed position of the valve in accordance with FIG. 2;

FIG. 5 longitudinal section through a blood collecting valve with an output structure, which is connected with an input structure by means of a screw seat, in a closed position;

FIG. 6 side view of the output structure of the blood collection valve in accordance with FIG. 5;

FIG. 7 longitudinal section corresponding to FIG. 5, however, the blood collecting valve in accordance with FIG. 5 in opened position;

FIG. 8 longitudinal section through a blood collecting device with an input structure with valve seat and an output structure being shaped as a valve element, in a closed position;

FIG. 9 plan view of the valve element in the blood collecting valve in accordance with FIG. 8; and FIG. 10 longitudinal section in accordance with FIG. 8, however illustrating the valve in accordance with FIG. 8 in an opened position.

WAYS FOR PERFORMING THE INVENTION

The blood taking valve 10 which is illustrated in FIG. 1, among others, corresponds in this structure of the valve which will be disclosed in more detail in the following in conjunction with FIGS. 2 to 4. It is provided with an input structural part 11.1 and an output structural part 12.1 which are mounted rotatably within each other and opposite each other. The supporting part 13 of a cannula is insertable into the input structural part 11.1. The application conus 15 of a blood collecting cylinder 16 is insertable into the output structural part 12 12.1. The term "conus" as used throughout this Specification and the Claims means a conical shaped opening or projection as the particular usage implies and includes the well known tapered luer surfaces commonly used on medical devices for fluid tight connections.

The supporting part 13 may be provided at the end of a catheter instead of a cannula 14. Instead of a blood collecting cylinder 16 an injection element with an application conus 15 may be inserted into the output structural part 12.1, namely if any solution should be injected into the circular system, instead of taking blood.

The structure of the blood collecting valve 10 in accordance with FIG. 4 will now be explained in detail in conjunction with FIGS. 2 to 3. Its input structural part 11.1 is shaped circularly with an upper and lower part, whereby the diameter of the upper part is less than the lower part. A separating wall 17 with half moon shaped separating wall opening 18 is provided at about the center of the length of the upper part. The output structural part 12.1 is so shaped that it is insertable very snug fitting in the input structural part from the side with the largest diameter thereof. With its upper sealing face 19 it the engages at the lower side of the separating wall 17. These two faces are pushed together in such a manner that at the lower end of the input structural part 11.1 a circumferential rib 20 which protrudes inwardly, behind which the output structural part 12.1 snaps in when it is pushed into the input structural part 11.1 to such an extent that sealing face 19 engages on the separating wall 17. Therefore, a structure is provided which is similar to a lever-water armature with a flat seal. Moreover, the input structural part 11.1 and the output structural part 12.1 are sealed off with respect to each other, in that an 0-ring 21 is provided on the outer circumference of the output structural part 12.1. The output structural part 12.1 is centrically penetrated by an inner conus 22 which is adaptably shaped with respect to application conus 15 on the blood collecting cylinder 16 or a syringe element. The end of the inner conus 22 is terminated by a half moon shaped seal face opening 23.

The blood collecting cylinder 16 is connected with the blood collecting valve 10 in that the application conus 15 is firmly inserted into the inner conus 22. In view of the very small opening angle of the conuses the application conus 15 rests relatively firm in the inner conus 22 after being inserted. Canula 14 together with its supporting part 13 is screwed into a thread 24 which is provided above the separating wall 17 on input structural part 11.1.

If blood should be taken starting from the closed position of the blood collecting valve 10 in accordance with FIG. 2 with applied canula 14 and applied blood collecting cylinder 16, the structural output part 12.1 should be turned by about 180° with respect to the structural input part 11.1. This turning is performed in that the outer wall of the structural input part 11.1 is held with two fingers of the one hand and the structural output part 12.1 is turned over the blood collecting cylinder 16. The structural input part 11.1 and structural output part 12.1 do assume the position illustrated in FIG. 4, wherein the separating wall opening 18 overlaps with the seal face opening 23. When the two structural parts are again turned by 180 degree in the opposite direction then the two mentioned openings are again separated from each other by an overlapping face 25 (FIG. 2) and are disposed adjacent to each other seen in flow direction.

The turning of the structural output part 12.1 with respect to the structural input part 11.1 is limited in that on the structural input part 11.1 at the lower part an inwardly extending nose 26 is provided which engages into a groove 27 extending over a circumferential angle of 180° degree in the structural output part 12.1, as is illustrated in FIG. 3.

In the second embodiment of a blood collection valve 10 in accordance with FIGS. 5 to 7 a cylinder like structural input part 11.2 is provided with a separating wall 17 which is provided with separating wall openings along its circumference and which centrically supports on its lower side a rubber gasket disk 28. Above the separating wall 17 a thread 24 is provided for screwing in the supporting element 13 of a cannula 14 or a catheter. Below the separating wall 17 two inwardly protruding thread guide teeth 30 are tipstretched.

The structural output part 12.2 is shaped as a cylindrical element with a centric inner conus 22. The upper face of the structural output part 12.2 extends to the inner conus 22 slightly upwardly, whereby a sealing edge 31 is formed on the inner conus 22. Two threads 32 extend in the outer circumferential wall of the structural output part 12.2 being engaged by one of the two thread guide teeth 30. The direction of the pitch of the threads 32 is so dimensioned that the structural output part 12.2 moves to the separating wall 17 when the structural output part 12.2 is turned to the right with respect to the structural input part 11.2. When the sealing edge 31 reaches the rubber sealing disk 28 during this twisting it seals the inner conus 22 with respect to the separating wall openings 18. If the two structural parts are turned further after the first sealing position the sealing edge 31 pushes more-strongly into the rubber sealing disk 28 and the thread guide teeth 30 finally reach the end of the associated thread 32. A small recess is provided in the direction to the separating wall 17 at the end of each thread 32 into which one of the thread guide teeth 30 snaps into when the end of the turnability is reached. The depth of the recesses 33 is only so small that during the snapping in of teeth 30 into these recesses the sealing edge 31 does not release from its sealing contact with the rubber sealing disk 28 and thereby also prevents a return snapping of the structural output part 12.2 with respect to the separating wall. For a turning in the counter direction the structural input part 11.2 and the structural output part 12.2 are at first pushed against each other axially to such an extent that each of the thread guide teeth 30 disengages again from the associated recess 33. It can then be turned to such an extent until each of the teeth 30 reaches the other end of the associated thread 32. This position, wherein a passage exists between the inner conus 22 and the separating wall openings 18 is illustrated in FIG. 7.

The recesses 33 may be eliminated if the structural output part 12.2 is guided selflocking with respect to the structural inner part 11.2. This is performed in that the pitch of the threads 32 is selected only very slight. The effect of selflocking is reinforcable in that the rubber seal disk 28 is shaped relatively soft with a low sliding surface so that the sealing edge 31 adheres somewhat on sealing disk 28 when it is pushes against it, so that the return movement of the structural output part 12.2 is prevented without exerting outside force.

In the embodiments of a blood collection valve 10 in accordance with FIGS. 8 to 10 the structural input part 11.3 is shaped as the valve seat element and the structural output part 12.3 as the valve element. The structural input part 11.3 consists of an upper hollow cylindrical separating wall part 34 and a lower cylindrical inner conus part 35 with a centrical inner conus 22. A hollow space exists between the lower side of the separating wall 17 and the upper side of the inner conus part 35 into which a structural output part 12.3 in form of a valve plate with a return spring is inserted before the connecting of the separating wall part 34 with the inner conus part 35. The structural output part 12.3 is provided with a lower valve plate 36, an upper guide ring 37 and a leaf like return spring 38 which connects these parts into one unit. The guide ring 37 engages on the lower side on separating wall 17. Without the influence of further forces the valve plate 36 is supported on an 0-ring 21 which encompasses the opening of the inner conus 22 in the upper side of the inner conus part 35.

The diameter and length of the inner conus 22 in the the inner conus part 35 are so dimensioned that a firmly inserted application conus 15 (see FIG. 9) in the inner conus 22 extends with its front end beyond the upper side of the inner conus part 35 into the space between this upper side and the lower side of the separating wall 17.

As long as no application conus 15 is inserted into the inner conus 22, the valve plate 36 supports sealingly on 0-ring 21 in the upper side of the inner conus part 35 (FIG. 8), whereby the output 40 of the blood collecting valve 10 is separated from input 39. However, as soon as an application conus 15 is totally inserted into the inner conus 22 (FIG. 9) the same pushes on the valve plate 36 and tilts the same, whereby the same releases the inner conus opening 41, so that blood may flow into this opening 41 flowing from input 39 and penetrating the separating wall openings. Conversely, one could, when the application conus 15 is mounted on an injection element, feed a solution through the inner conus opening 41 and the separating wall openings 18 to the input 39. As soon as the application conus 15 is again removed from the inner conus 22 the valve plate 36 again supports engagingly on the 0-ring 21 in the upper side of the inner conus part 35.

The hitherto mentioned embodiments were based on that a thread 24 was provided on the side of input 39 of each structural input part 11.n for screwing in the supporting part 13 of a canula 14 or a catheter. Instead, the structural input parts may be formed on the input side in accordance with the shape of an application conus 15 of a blood collecting cylinder 16.

In the embodiment of a blood collection valve 10 in accordance with FIGS. 1 to 4 two half moon shaped openings are brought into congruence with each other by turning against each other or are again sealingly separated from each other. Such a bringing into congruence or separating again from each other may be performed by a common displacement between a structural input part and a structural output part in a lineal direction, instead of turning.

In all embodiments of the inventive blood collection valves it is advantageous when an abutment for limiting the movements is provided in the manner that a displacement is restricted in the first direction as soon as the valve is maximally opened and the displacement is restricted in the counter direction as soon as the valve is totally closed.

It is of a particular advantage to make all parts of an inventive blood collecting valve from a physiological compatible synthetic, that is, materials being used in the medical technology for disposal in the customary manner.

So that the user knows everytime whether the blood collection valve is in a opened or closed stage, it is advantageous to provide corresponding markings on the structural input part and on the structural output part, for example, lines which in the opened stage align and which are turned away from each other in the closed stage.

I claim:

1. A valve structure for placement between a tube to introduce or take fluid from a vessel and a device to collector or supply fluid to a vessel, comprising;
   an input part having a circular passage therethrough aligned along an axis thereof for connection with a tube to introduce or take fluid from a vessel;
   a separating wall located across part of the circular passage, the separating wall having an opening therethrough;
   an output part configured with a circular surface for insertion into the circular shaped passage when aligned along the axis and the circular surface designed for engagement with while moveable relative to the circular passage;
   a structural part on the output part positioned to cooperate with the input part and control axial and rotary movement of the output relative to the input part;
   an inner conus passing through the output part, the inner conus shaped to engage with an application conus on a device to collect or supply fluid forming a removable fluid tight connection; and
   a valve means operatively and physically associated with the input and output parts and positioned concentric to the axis near where the input and output parts engage one another to connect and disconnect the passage in the input part with the device of the output part, the valve means movably operative relative to the input and output parts and the output part being movable upon engagement of the application conus with inner conus.

2. The valve structure of claim 1 wherein the input part has an upper circular part and a lower circular part with a separating wall therebetween, the upper circular part for connection to introduce or take fluid from a vessel.

3. The valve structure of claim 2 wherein the valve means includes an opening in a portion of the separating wall for connecting between the upper and lower circular parts.

4. The valve structure of claim 3 wherein the output part is shaped to be inserted into the lower circular part and the valve means includes an upper sealing face on the output part for moveable engagement with the separating wall.

5. The valve structure of claim 4 wherein the valve means has a sealing opening passing through a portion of the upper sealing face, the sealing opening is configured for selective alignment with the opening in the separating wall upon relative movement of the parts.

6. The valve structure of claim 5 wherein the output part includes a circular shape to insert along the axis into the lower circular part for engagement so that the circular parts rotate relative to one another aligning or closing the opening and the sealing opening to allow or prevent fluid passage.

7. The valve structure of claim 6 wherein the opening and the sealing opening are each half-moon shaped and concentrically positioned relative to the axis of rotation relative to one another aligning or closing the opening and the sealing opening to selectively permit fluid passage by rotation of the input and output parts relative to one another while maintaining the fluid tight connection of the application conus and the inner conus.

8. The valve structure of claim 1 wherein the valve means includes circumferential openings in the separating wall.

9. The valve structure of claim 8 wherein the valve means has a rubber gasket for sealing against the lower side of the separating wall.

10. The valve structure of claim 9 wherein the valve means includes a sealing edge on the output part for engagement of the rubber gasket to close the passage upon relative axial movement of the input and output parts.

11. The valve structure of claim 6 wherein the input and output parts have threads for cooperative rotary engagement to move the input and output parts axially relative to each other to permit the engagement and disengagement of the sealing edge and the gasket.

12. The valve structure of claim 1 wherein the inner conus is conical to receive the application conus on a device for collecting or supplying fluid to a vessel.

13. The valve structure of claim 3 wherein the output part is shaped to be inserted into the lower circular part of the input part, the output part having a valve plate for closing the inner conus.

14. The valve structure of claim 13 wherein the valve plate is located along the axis between the separating wall and the inner conus and the valve plate are resiliently biased in the closed position.

* * * * *